United States Patent
Wolfe et al.

(10) Patent No.: US 7,790,688 B2
(45) Date of Patent: Sep. 7, 2010

(54) COMPOSITIONS AND METHODS FOR INCREASING MUSCLE MASS, STRENGTH, AND FUNCTIONAL PERFORMANCE IN THE ELDERLY

(75) Inventors: Robert Wolfe, Little Rock, AR (US); John Troup, Plymouth, MN (US); Nicolaas ("Mick") Emile Paulus Deutz, Little Rock, AR (US)

(73) Assignee: HealthSpan Solutions, LLC, Little Rock, AR (US)

( * ) Notice: Subject to any disclaimer, the term of this patent is extended or adjusted under 35 U.S.C. 154(b) by 62 days.

(21) Appl. No.: 12/013,269

(22) Filed: Jan. 11, 2008

(65) Prior Publication Data

US 2009/0181903 A1    Jul. 16, 2009

(51) Int. Cl.
  *A01N 43/04*   (2006.01)
  *A61K 31/70*   (2006.01)
(52) U.S. Cl. .......................... 514/23; 426/656
(58) Field of Classification Search ................ None
  See application file for complete search history.

(56) References Cited

U.S. PATENT DOCUMENTS

| 6,028,107 | A  | * | 2/2000  | Waugh ................ 514/563 |
| 6,200,601 | B1 |   | 3/2001  | Gorenbein et al. |
| 6,525,027 | B2 |   | 2/2003  | Vazquez et al. |
| 2004/0248771 | A1 | * | 12/2004 | Raggi .................... 514/2 |
| 2005/0002992 | A1 |   | 1/2005  | McCleary et al. |
| 2005/0106218 | A1 |   | 5/2005  | Ward et al. |
| 2007/0015686 | A1 |   | 1/2007  | Heuer et al. |
| 2008/0038320 | A1 |   | 2/2008  | Oommen et al. |
| 2008/0114066 | A1 |   | 5/2008  | Johnson et al. |

FOREIGN PATENT DOCUMENTS

WO    2006116755 A2    11/2006

OTHER PUBLICATIONS

International Search Report, International Application No. PCT/US08/87956, mailed on Aug. 5, 2009, 13 pages.

* cited by examiner

*Primary Examiner*—Patrick T Lewis
(74) *Attorney, Agent, or Firm*—Lewis, Rice & Fingersh, L.C.

(57) ABSTRACT

Compositions and methods for increasing muscle mass, strength, and functional performance in the elderly by delivering a selection of amino acids, carnitine, and carboydrates with a low glycemic index.

21 Claims, 7 Drawing Sheets

Pathways of RNA synthesis. BSP, base salvage pathway; DNP, de novo base synthesis pathway; RSP, ribonucleoside salvage pathway.

Values are averages over 1 h after ingestion

COMPOSITIONS AND METHODS FOR INCREASING MUSCLE MASS, STRENGTH, AND FUNCTIONAL PERFORMANCE IN THE ELDERLY

BACKGROUND

1. Field of the Invention

The present invention generally relates to compositions and methods for increasing muscle mass, strength, and functional performance in the elderly. In particular, the compositions consist of a selection of amino acids including leucine, carnitine, and carbohydrates with low glycemic index.

2. Description of the Related Art

As the population ages, and in particular as the "baby boomers" grow into their old age, the health problems associated with aging grow increasingly important This is particularly true in a health system such as the current one where health care costs are distributed across the population; the increased prevalence of aging-related health problems will result in generally increased costs to all. In addition, reactive health care is more expensive than preventative health care; for example, fixing broken bones or replacing a hip after a fall by a frail patient is more expensive than preventing that fall by decreasing the patient's frailty. For these and other reasons, it is desirable to have effective, relatively inexpensive means for preventing and ameliorating some aging-related health problems.

One such health problem may be referred to as "sarcopenia." As used herein, the term "sarcopenia" refers to the loss of muscle mass and function that inevitably occurs with aging. Sarcopenia is responsible for decreased levels of physical activity which, in turn, can result in increased body fat and a further loss of muscle. Loss of muscle mass results from a negative net balance between muscle protein synthesis and muscle protein breakdown. The etiology of this loss of skeletal muscle mass and function is not believed to be clear. Reduced levels of physical activity, loss of motor units secondary to changes in the central nervous system, and inadequate protein intake have all been implicated.

Sarcopenic individuals, in their relatively weaker state, may be more prone to falls and injuries from performing bodily tasks that may have been performed more easily when they had greater muscle mass and function. They also may have decreased bone and joint health, which further limits mobility. Because sarcopenia increases risk of injury, decreases mobility and quality of life, and causes other problems, it is desirable to effectively, noninvasively, and relatively inexpensively prevent or ameliorate sarcopenia and increase muscle mass, strength, and physical function, especially in the elderly.

Stimulation of muscle protein synthesis is believed to be the metabolic basis for increased muscle strength. An increase in muscle protein synthesis can increase muscle mass, which is related to strength. Increasing muscle protein synthesis also increases muscle protein turnover (i.e., the combination of protein synthesis and breakdown), since the rate of breakdown is believed to be related to the rate of synthesis to some extent. Increased muscle protein turnover increases the functioning of muscle fiber units, because the older, damaged proteins are replaced by newly produced proteins that function more efficiently. Thus, a method to increase muscle protein synthesis and muscle protein turnover may achieve the goal of increasing muscle mass, strength, and physical function.

There are believed to be four central components to the stimulation of muscle protein synthesis. The capacity of the synthetic apparatus of the cell must be activated by a series of factors collectively referred to as eukaryotic initiation factors. The availability of all the component amino acids needed for the synthesis of the new proteins must be increased, and transfer RNA (tRNA) molecules must transfer those amino acids effectively from the intracellular free pool to the site of synthesis in the ribosome. Finally, there must be adequate energy available, in the form of adenosine-triphosphate (ATP), for all the necessary reactions to proceed. In sum, increased physical function requires not only adequate muscle mass and function of the muscle fibers, but also the energy needed to support muscle contraction. Energy can be stored in the cell as ATP and creatine-phosphate (CP). Synthesis of ATP is believed to be promoted by the provision of ribose, and creatine is believed to promote the storage of energy in the form of CP.

By addressing any or all of these four components, muscle protein synthesis can be increased either pharmacologically or through nutrition. Pharmacological interventions (e g, testosterone) can be effective, but all have significant undesirable side effects and require medical supervision. In contrast, nutritional compositions are desirable because they are noninvasive and may be designed to minimize such side effects, and may become a part of an individual's routine without such medical supervision.

There are currently no nutritional compositions designed to specifically promote muscle protein synthesis in elderly individuals, or more generally to improve strength and functional performance in elderly individuals. Current nutritional compositions are not believed to have sufficient leucine to effectively accomplish the goals stated herein, alone or in combination with muscle-building compounds such as creatine. For example, whey isolates currently comprise between about 6 and about 9% leucine; this is not believed to be sufficient to achieve improved muscle mass, strength, and functional performance in the elderly.

A high percentage of elderly individuals suffer some degree of renal insufficiency, often at the sub-clinical (and thus undiagnosed) level. Impaired renal function is common in individuals with sarcopenia, so nutritional approaches to resolving sarcopenia must not compound this potential problem by increasing the load of urea that the kidney must excrete. A high intake of protein could potentially amplify this problem by causing a significant increase in urea production, thereby putting an increased burden on the kidney by requiring increased urinary excretion. It is therefore desirable for any composition for supporting synthesis to minimize renal burden.

The effect of increased protein intake on bone health has been debated. On the one hand, protein synthesis is essential for bone health and is stimulated by increased protein intake. Since collagen is a major protein component of bone and glycine constitutes about 30% of collagen, it is desirable for a composition promoting bone synthesis to contain sufficient glycine and other amino acids to stimulate collagen synthesis in bone. On the other hand, ingestion of sulphur-containing amino acids, particularly cystine and cysteine, causes the production of sulfuric acid in the course of their metabolism. Increased sulfuric acid acidifies the blood and accelerates loss of calcium from bone. It is therefore desirable for such a composition to circumvent this response by not including either cystine or cysteine, as neither of these amino acids is believed to be necessary for stimulation of muscle protein synthesis.

An additional difficulty with nutritional supplements for older adults is that older adults generally compensate for increased energy (i.e., calories) delivered by nutritional supplements by reducing food intake. It is therefore desirable to design a supplement that stimulates muscle synthesis more efficiently than food or common protein supplements.

SUMMARY

Because of these and other problems in the art, disclosed herein are compositions and methods for increasing muscle mass, strength, and functional performance in the elderly by delivering a selection of amino acids, carnitine, and carboydrates with a low glycemic index.

There are described herein compositions of matter for increasing muscle mass, strength, and functional performance, comprising leucine, carbohydrate, and creatine.

There are also described herein compositions of matter for increasing muscle mass, strength, and functional performance, comprising leucine, other amino acids, carbohydrate, and creatine; wherein the other amino acids are selected from the group consisting of histidine, isoleucine, valine, lysine, methionine, phenylalanine, threonine, arginine, glycine, carnitine, and citrullene.

In an embodiment of such compositions, the other amino acids may comprise histidine, isoleucine, valine, lysine, methionine, phenylanlanine, threonine, glycine and arginine, or histidine, isoleucine, valine, lysine, methionine, phenylalanine, threonine, glycine and citrullene.

In an embodiment of such compositions, the carbohydrate comprises ribose.

In an embodiment of such compositions, the leucine comprises a percentage of the composition by mass between about 10 and about 25 percent, more preferably about 11 and about 20 percent.

In an embodiment, such a composition is a component of means for liquid administration.

In a still further embodiment, the composition further comprises an excipient.

There is also described herein a method of increasing muscle mass, strength, and functional performance, comprising: having a patient; and delivering to the patient a composition of matter comprising leucine, carbohydrate, and creatine.

In an embodiment of the method the patient is elderly and the method of delivering may be oral, such as through liquid administration.

In another embodiment of the method, the composition further comprises other amino acids selected from the group consisting of histidine, isoleucine, valine, lysine, methionine, phenylalanine, threonine, arginine, glycine, carnitine, and citrullene.

In a still further embodiment of the method, leucine comprises a percentage of the composition by mass between about 10 and about 25 percent, more preferably between about 11 and about 20 percent.

In a still further embodiment of the method, the composition further comprises an excipient and the carbohydrate comprises ribose.

There is also described herein a method of increasing muscle mass, strength, and functional performance in the elderly, comprising: generating a composition of matter comprising leucine, carbohydrate, and creatine; providing to an elderly patient the composition of matter.

In an embodiment of the method the composition further comprises other amino acids selected from the group consisting of histidine, isoleucine, valine, lysine, methionine, phenylalanine, threonine, arginine, glycine, carnitine, and citrullene.

In a still further embodiment of the method the leucine comprises a percentage of the composition by mass between about 10 and about 25 percent, more preferably between about 11 and about 20 percent.

In a still further embodiment of the method the providing is oral, such as by liquid administration.

In a still further embodiment of the method, the carbohydrate comprises ribose.

DESCRIPTION OF PREFERRED EMBODIMENTS

Figure 1:
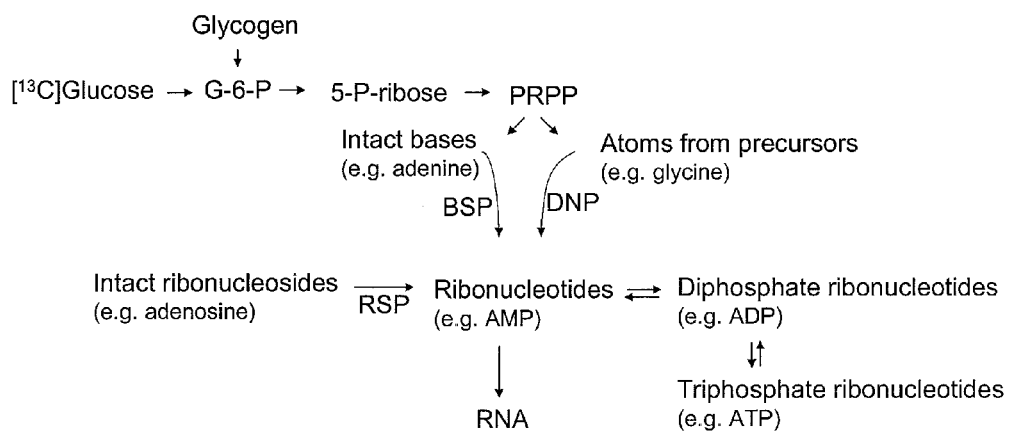
FIG. 1 shows the metabolic pathways for the synthesis of RNA and how ribose and glycine are believed to serve as precursors for the production of new RNA.

Strength and physical function, including mobility, may be improved by increasing muscle mass and function and improving bone and joint health by stimulating muscle protein synthesis. Disclosed herein are compositions and methods that increase muscle protein mass, strength and physical function in those with sarcopenia, including but not limited to the elderly or individuals over 60 years of age. The compositions generally consist of a blend of amino acids, including leucine, and carbohydrates in which the proportion of each amino acid and the amount of carbohydrate is tailored to optimize muscle protein synthesis and muscle protein turnover, and consequently increase muscle mass, strength and physical function. The compositions may also or alternatively comprise creatine.

Generally, the new composition addresses all the aspects of protein synthesis. The eukaryotic initiation factors are activated by the amino acid leucine. The availability of the essential amino acids not produced by the body will be increased by ingestion of the composition. The non-essential amino acid component of the newly synthesized protein may be derived from available pools resulting from protein breakdown or de novo synthesis. The availability of tRNA may be increased by ingestion of ribose and glycine, key precursors for nucleotide synthesis, and stimulation of tRNA synthesis by the ingested amino acids. Energy may be provided by low-glycemic carbohydrates that may induce a minimal insulin response. In an embodiment, such energy is provided in the exact amount needed. Protein synthesis may be increased by the provision of key amino acid precursors and also by stimulation of the synthesis of transfer-ribonucleic acid (tRNA), which governs a rate-limiting step in protein synthesis. Function will be enhanced by increasing the energy stores within muscle.

The compositions and methods may also minimize the renal burden. Ingestion of a high proportion of the essential amino acids not produced in the body (i.e., essential amino acids, or EAAs) will cause a diminished availability of alanine and glutamine, the two principal ureagenic amino acids. Alanine and glutamine will be reincorporated into protein at a greater rate by the provision of essential amino acids, and urea production will not increase, and may actually decrease. Renal function may be preserved by minimizing urea production through the suppression of transport of the primary ureagenic amino acids alanine and glutamine to the liver by instead stimulating their reincorporation into protein.

The rationale underlying the compositions disclosed herein relates to both the individual effects of the components and their interactive effects. The amino acids will stimulate muscle protein synthesis. The particular essential amino acids are provided because they cannot be produced in the body and are thus their availability is rate-limiting for protein synthesis. Arginine is normally produced in adequate quantities in the body, but endogenous production may be limited in elderly. Glycine is also produced in the body, but in limited amounts; it is believed that extra glycine may stimulate synthesis of tRNA as well as collagen in tendons and ligaments. Citrullene can be used as a precursor for arginine to increase the plasma arginine level. Cystine and cysteine, as well as other sulfur-containing amino acids, may be excluded in order to avoid detrimental effects on bone health. Amino acids may be included in the free form; in combinations of peptides; in combinations of intact protein and free amino acids; in combinations of free amino and peptides; or in combinations of free amino acids, peptides, and proteins. Their delivery method and quantity is such that there is no undue renal burden.

One or more low glycemic carbohydrates may provide the energy needed to produce the new protein without eliciting a significant insulin response. This energy source may also drive muscle growth more efficiently than food or other protein supplements in order to achieve muscle synthesis without causing users or patients to compensate for increased calorie intake. Such compounds, which may also be referred to as slow release saccharides, may include complex carbohydrates with long carbon chain lengths, including but not limited to nutriose, sucramalt, isomaltulose, dextrans, maltodextran, and their functional equivalents. The elderly are generally resistant to the action of insulin, so avoiding an insulin response by using low glycemic carbohydrate will be advantageous to that population.

In addition to or alternatively to a low glycemic carbohydrate or slow release saccharide, the composition may comprise ribose. Ribose may increase the amount of tRNA, which will be useful when combined with increased availability of the rate-limiting amino acids provided in this embodiment. The metabolic pathways by which glycine and ribose may stimulate RNA synthesis are shown in FIG. 1. Because of the similar functionality of low glycemic carbohydrates, slow release saccharides, and ribose in the compositions and methods disclosed herein, the term "carbohydrate" used herein may refer to all these compounds. Low glycemic carbohydrate may comprise about 0-50% by mass. About two times the carbohydrate as total amino acids may be added, as this will provide the exact amount of energy needed for the stimulation of muscle protein synthesis resulting from the amino acids. An embodiment of such a calculation is disclosed below in Example 10. In a preferred embodiment, about 25, 26, 27, 28, 29, or 30 g of carbohydrate may be added. These embodiments are based on the energy requirement of protein synthesis resulting from the amino acids, and the amount of energy supplied by the carbohydrate. Close matching of these two values yields the minimal amount of carbohydrate for maximal functionality.

Creatine is believed to increase muscle mass and improves strength by increasing energy stores in the muscle, and therefore may be a component of a composition for increasing muscle mass. When such components (i.e., essential amino acids, low glycemic carbohydrates, and creatine) are coupled together in a preferred embodiment, muscle strength, mass, and physical function will be increased to a greater extent than predicted by the response to any one component.

One embodiment encompasses a composition comprising L-histidine, L-isoleucine, L-leucine, L-valine, L-lysine, L-methionine, L-phenylalanine, L-threonine, L-arginine, carbohydrate with low glycemic index, and α-methyl guan-dino-acetic acid, or creatine.

Another embodiment encompasses a composition comprising of L-histidine, L-isoleucine, L-valine, L-lysine, L-methionine, L-phenylalanine, L-threonine, L-citrullene, carbohydrate with low glycemic index, and creatine.

As explained, leucine is believed to activate the eukaryotic initiation factors of protein synthesis. In an embodiment, the concentration of L-leucine by mass is greater than about 6% of the amino acid component. In a preferred embodiment the concentration of L-leucine is between about 10 and about 40%. In a more preferred embodiment, the concentration of L-leucine is between about 10 and about 25%. In a most preferred embodiment, the concentration of L-leucine is between about 11 and about 20%.

The concentrations of the other amino acids may be in any proportion to optimize muscle protein synthesis. Citrullene may range from about 0-10%, arginine may range from about 0-10%, and carnitine may range from about 0-15% by weight of amino acids. The concentration of L-histidine in the composition may be about 9%, 10%, 11%, 12%, or 13% by weight of the amino acids. The concentration of L-methionine in the composition may be about 3%, 3.5%, or 4% by mass of the amino acids. The concentration of L-phenylalanine in the composition may be about 13%, 14%, 15%, 16%, or 17% of the amino acids by mass. The concentration of L-threonine in the composition may be about 13%, 14%, 15%, 16%, or 17% of the amino acids by mass. The concentration of L-valine may be between about 10-12% by mass of the amino acids. The concentration of L-isoleucine may be about 9%, 10%, 11%, or 13% by mass of the amino acids. The concentration of L-lysine in the composition may be about 9%, 19%, 11%, or 12% of the amino acids by mass. The L forms of the amino acids are the naturally occurring isomers normally present in the body.

In a preferred embodiment, the following components have the following percentages of the total amino acids by mass: histidine, about 6.4; isoleucine, about 6.2; lysine, about 11.0; methionine, about 2.0; phenylalnine, about 11.0; threonine, about 9.5; tryptophan, about 0.4; valine, about 7.3; glycine, about 3.8; citrullene, arginine, or a combination thereof, about 3.0, and leucine, the remainder. In a further preferred embodiment, these components total to 20 g of total amino acids.

In a further preferred embodiment, creatine may comprise about 8.0% of the composition by mass. Carbohydrates may comprise about twice the total mass of histidine, isoleucine, leucine, lysine, methionine, phenylalanine, threonine, tryptophan, and valine. Ribose may comprise about ten percent of those carbohydrates. It is contemplated that food science requirements may require altering the percentages from these values.

In another embodiment carnitine may range from about 0-10% by mass of the amino acids, and arginine may range from about 0-10% of the amino acids. Leucine may range from about 23-30% by mass of the amino acids, and the low glycemic carbohydrate may range from about 0-50% of the total mass. The other amino acids may be in proportion to optimize muscle protein synthesis In another embodiment, wherein the taste of the composition may be improved without compromising efficacy, citrulline may range from about 0-10% by mass of the amino acids, and arginine may be excluded. Camitine may range from about 0-15% of mass of amino acids, L-leucine may range from about 18-30% by mass of the amino acids, and the low glycemic carbohydrate may range from 0-50% by mass.

In addition to the amino acid selection, the great quantity of amino acids delivered in the compositions and methods disclosed herein also increases muscle strength, mass, and physical function. It is believed that greater total amounts or percentages of protein, and greater amounts or percentages of essential amino acids, particularly leucine, will contribute to greater health effects. In a preferred embodiment, about 20 g of amino acids are delivered, with about 11 to about 20 percent of those 20 g being leucine.

In alternative or further embodiments, supplemental minerals may also be included. Suitable minerals may include one or more minerals or mineral sources. Non-limiting examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

The compositions may also optionally comprise vitamins. The vitamins may be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

The composition may also comprise at least one excipient. Non-limiting examples of suitable excipients include a buffering agent, a preservative, a stabilizer, a binder, a compaction agent, a lubricant, a dispersion enhancer, a disintegration agent, a flavoring agent, a sweetener, a coloring agent, and combinations of any of these agents.

In an embodiment, the excipient is a buffering agent. Non-limiting examples of suitable buffering agents include sodium citrate, magnesium carbonate, magnesium bicarbonate, calcium carbonate, and calcium bicarbonate.

The excipient may comprise a preservative. Suitable examples of preservatives include antioxidants, such as alpha-tocopherol or ascorbate, and antimicrobials, such as parabens, chlorobutanol, or phenol.

In an alternative or further embodiment, the excipient may be a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In an alternative or further embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In yet another embodiment, the excipient may be a disintegrant. The disintegrant may be a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. The disintegrant may be an effervescent disintegrant. Suitable effervescent disintegrants include sodium bicarbonate in combination with citric acid, and sodium bicarbonate in combination with tartaric acid.

The excipient may include a flavoring agent. Flavoring agents incorporated into the outer layer may be chosen from synthetic flavor oils and flavoring aromatics; natural oils; extracts from plants, leaves, flowers, and fruits; and combinations thereof. By way of example, these may include cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

It may be desirable to provide a coloring agent. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants, may be suitable for use in certain embodiments.

The weight fraction of the excipient or combination of excipients in the formulation may be about 30% or less, about 25% or less, about 20% or less, about 15% or less, about 10% or less, about 5% or less, about 2%, or about 1% or less of the total weight of the amino acid composition.

Also contemplated are methods of delivery of the compositions disclosed herein, including but not limited to dosage. The compositions disclosed or made obvious herein may be formulated into a variety of forms and administered by a number of different means. The compositions may be administered orally, rectally, or parenterally, in formulations containing conventionally acceptable carriers, adjuvants, and vehicles as desired. The term "parenteral" as used herein includes subcutaneous, intravenous, intramuscular, or intrasternal injection, or infusion techniques. In an exemplary embodiment, the compounds of the invention are administered orally.

Solid dosage forms for oral administration may include capsules, tablets, caplets, pills, troches, lozenges, powders, and granules. A capsule typically comprises a core material comprising a composition of the invention and a shell wall that encapsulates the core material. The core material may be solid, liquid, or an emulsion. The shell wall material may comprise soft gelatin, hard gelatin, or a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Some such polymers may also function as taste-masking agents.

Tablets, pills, and the like may be compressed, multiply compressed, multiply layered, and/or coated. The coating may be single or multiple. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. Tablets and pills may additionally be prepared with enteric coatings.

Alternatively, powders or granules embodying the compositions disclosed and made obvious herein may be incorporated into a food product. In a preferred embodiment, the food product may be a drink for oral administration. Non-limiting examples of a suitable drink include fruit juice, a fruit drink, an artificially flavored drink, an artificially sweetened drink, a carbonated beverage, a sports drink, a liquid diary product, a shake, and so forth. Other suitable means for oral administration include aqueous and nonaqueous solutions, emulsions, suspensions and solutions and/or suspensions reconstituted from non-effervescent granules, containing suitable solvents, preservatives, emulsifying agents, suspending agents, diluents, sweeteners, coloring agents, and flavoring agents.

The food product may also be a solid foodstuff. Suitable examples of a solid foodstuff include a food bar, a snack bar, a cookie, a brownie, a muffin, a cracker, an ice cream bar, a frozen yogurt bar, and the like.

The compositions of the invention may be utilized in methods to increase muscle mass, strength and physical function. In an embodiment, the method comprises administering the composition as described above twice per day between meals. The amount per dose may be about 10, 11, 12, 13, 14, 15, 16, 17, 18, 19, 20, 21, 22, 23, 24, 25, 26, 27, 28, 29, or 30 g. Alternatively, the composition may be administered one day per day, three times per day, or four times per day.

In an alternative or further embodiment of a method of delivery, the composition may also be used in conjunction with exercise. For example, the composition may given before or immediately after exercise.

The following examples provide embodiments of compositions, their use, and the effects of such use.

Example 1

Figure 2:
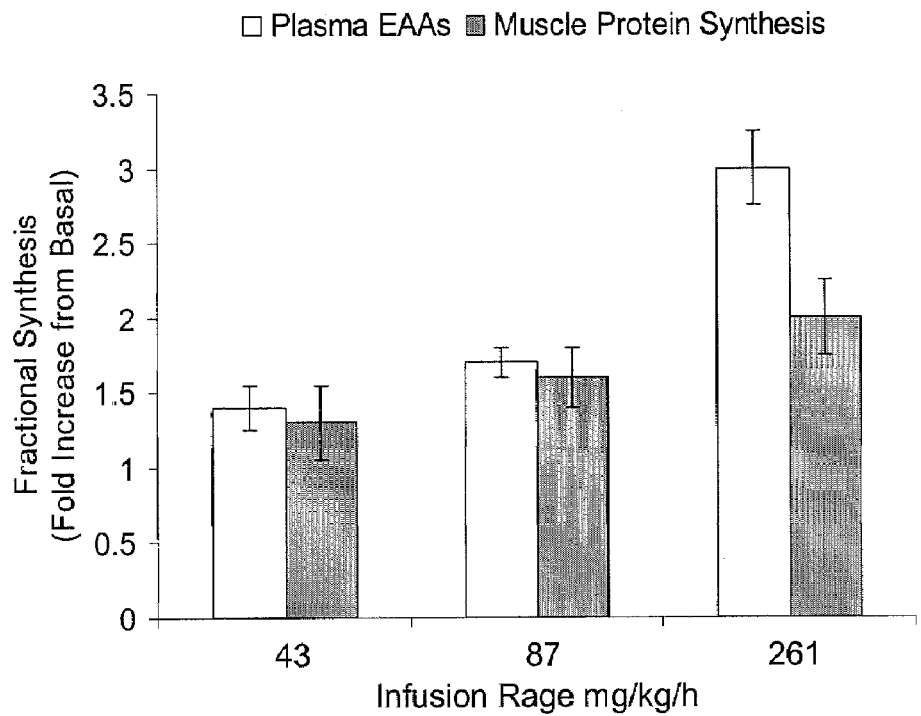
FIG. 2 shows results of infusing subjects with one of three doses of an embodiment of a composition for increasing muscle mass, strength, and functional performance.

The selection of the appropriate dose of the composition is important to maximize the effectiveness per gram ingested. Therefore a study was performed to relate the magnitude of stimulation of muscle protein synthesis to the extent of increase of plasma amino acid concentrations. Subjects were infused with one of three doses of amino acids to produce three distinct levels of plasma amino acids. The amino acids may be delivered as AMINOSYN® (a nutrient preparation containing amino acids). The results are highlighted in FIG. 2, which shows the relation between increase in plasma EAAs and FSR of muscle protein. Plasma EAA concentrations were increased by infusion of a commercially-available solution, Travasol®. Increases plasma EAA concentrations and muscle protein synthesis were all significant as compared to baseline. FSR at 87 and 261 mg/kg/h were significantly higher than at 43 mg/kg/h (P<0.05), but not different from each other.

When plasma essential amino acids (leucine, isoleucine, valine, histidine, lysine, metionine, threonine, phenylalanine) (EAAs) were increased by either about 35% or about 60%, there were proportionate increases in muscle protein FSR. However, when plasma EAAs were increased more than about 300%, muscle protein synthesis increased only slightly more. The relation between plasma EAA concentrations and muscle protein FSR was used to develop the dosage of EAAs in the proposed composition.

Example 2

Figure 3:
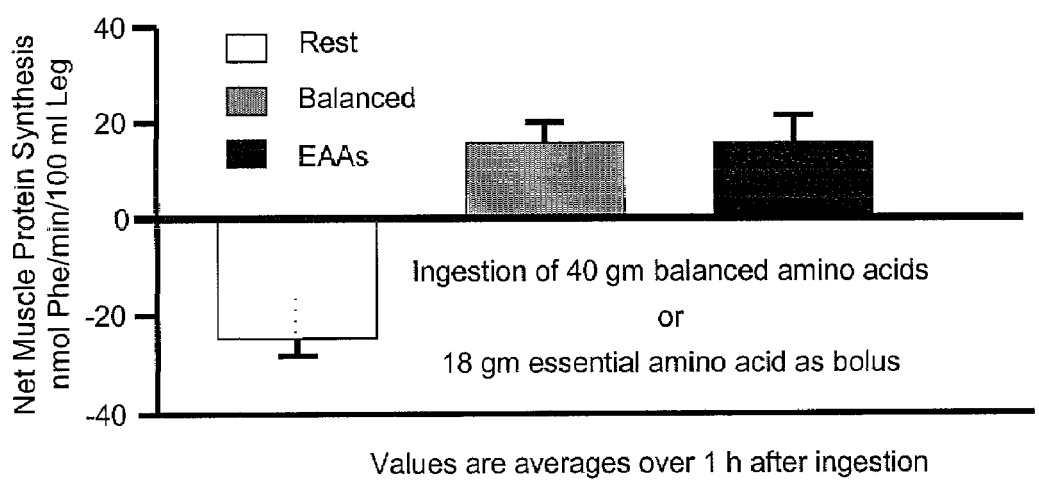
FIG. 3 shows responses of net muscle protein balance to ingestion of an embodiment of a composition for increasing muscle mass, strength, and functional performance.

The relative role of essential and non-essential amino acids on the stimulation of muscle protein anabolism in older adults was reviewed. In this case anabolism refer's to the difference between the rates of muscle protein synthesis and breakdown (i.e., net gain or loss of muscle protein). The response of muscle protein metabolism to a composition embodiment with about 18 g of essential amino acids (EAAs) was compared to the response to a composition embodiment with about 40 g of balanced amino acids (BAAs) (about 18 g EAA+about 22 g non-essential amino acids, NEAA) given orally to healthy older volunteers (BAA: n=8, age 71±2 yr; EAA: n=6, age 69±2 yr) (35) (FIG. 3). The amino acids were in the profile found in beef protein. FIG. 3 shows the response of net muscle protein balance to ingestion of about 40 gm of amino acids in the profile of beef protein, or the about 18 g of EAAs contained in the 40 gm mixture. Both formulations significantly improved net muscle protein balance due to a stimulation of muscle protein synthesis. Deletion of the non-essential amino acids did not adversely affect the response.

It was determined that phenylalanine net balance across the leg (corresponding to net muscle protein synthesis, or the balance between protein synthesis and breakdown) increased similarly from basal (p<0.01) in both groups (BAA: −16±5 to 16±4; EAA: −18±5 to 14±13; nmol·min$^{-1}$·100 ml leg$^{-1}$) due to a similar increase (p<0.01) in muscle protein synthesis (BAA: 43±11 to 67±11; EAA: 62±6 to 75±10; nmol·min$^{-1}$· 100 ml leg$^{-1}$) and no change in breakdown. In a separate example, ingestion of only non-essential amino acids (NEAAs) had no effect on muscle protein synthesis.

It was concluded that essential amino acids are solely responsible for the amino acid-induced stimulation of muscle protein anabolism in the elderly. Non-essential amino acids may therefore be withheld from nutritional supplements for sarcopenia. This observation provides the basis for an EAA-based supplement that is more efficient than normal food intake in terms of stimulation of muscle protein synthesis (see Example 4).

Example 3

Examples 1 and 2 demonstrate that amino acids stimulate muscle protein synthesis, yet a prior study showed that a high protein meal did not enhance myofibrillar protein synthesis in elderly individuals following resistance exercise. The hypothesis that altered sensitivity to the normally anabolic action of insulin impairs the normal interactive effects between glucose and amino acid intake on muscle protein synthesis was reviewed.

Figure 4:
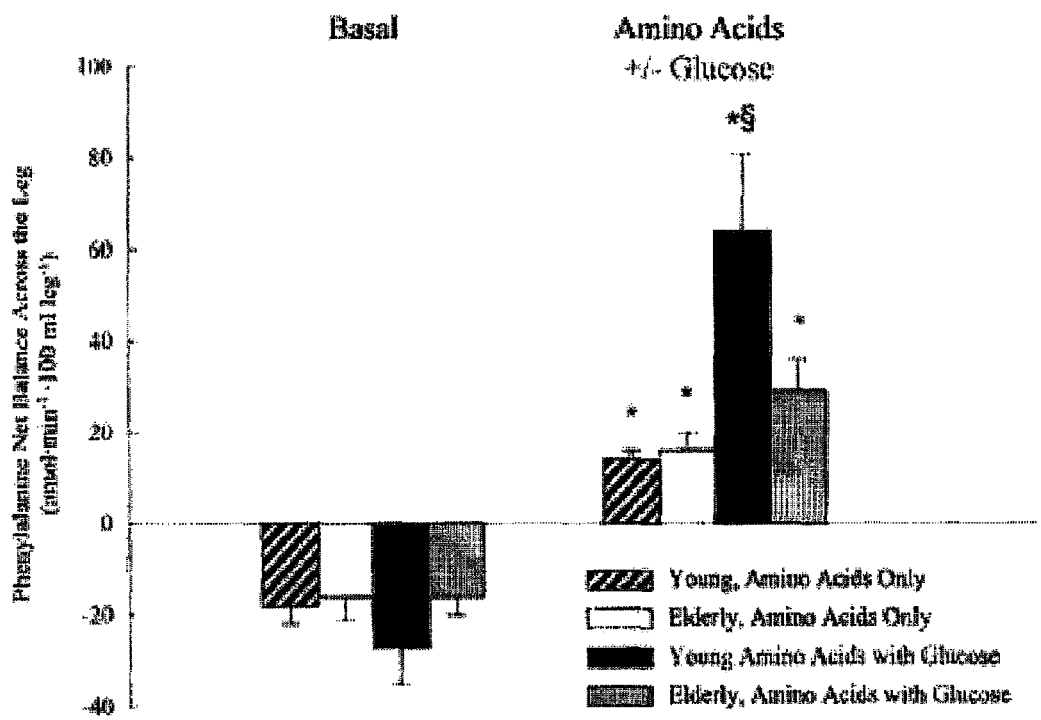
FIG. 4 shows a comparison of the effects of two embodiments of compositions for increasing muscle mass, strength, and functional performance on muscle protein anabolism in young and elderly subjects.

Muscle protein synthesis and breakdown was measured in healthy young (30±3 yr) and elderly (72±1 yr) volunteers in the basal postabsorptive state and during the administration of an amino acid-glucose mixture, using L-[ring-$^2$H5]phenylalanine infusion, femoral artery and vein catheterization, and muscle biopsies. Basal muscle amino acid turnover was similar in young and elderly subjects. The mixture increased phenylalanine leg delivery and transport into the muscle in both groups. Phenylalanine net balance increased in both groups (young, −27±8 to 64±17; elderly, −16±4 to 29±7 nmol/(min·100 mL); P<0.0001, basal vs. mixture), but the increase was significantly blunted in the elderly (P=0.030 vs. young). Muscle protein synthesis increased in the young, but remained unchanged in the elderly [young, 61±17 to 133±30 (P=0.005); elderly, 62±9 to 70±14 nmol/(min·100 mL) (P=S)]. In both groups, protein breakdown decreased (P=0.012) and leg glucose uptake increased (P=0.0258) with the mixture (FIG. 4). FIG. 4 shows a comparison of the effects of an amino acid-glucose supplement vs. the same amount of amino acids alone on muscle protein anabolism in young and elderly subjects. Phenylalanine net balance across the leg increased significantly during oral supplementation in all groups. However, compared with amino acids alone the addition of glucose to the supplement induced a significantly higher response in the young, whereas it did not add any benefit in the elderly. Values are the mean±SE. *, P<0.01 vs. basal; §, P<0.05 vs. others.

It was concluded that the response of muscle protein anabolism is impaired in healthy elderly individuals by a concomitant insulin response to carbohydrate intake. The practical implication of this result is that a dietary supplement to promote muscle protein synthesis in the elderly should not induce an insulin response. It is for this reason that a low glycemic carbohydrate may be used to provide energy and taste while eliciting a minimal insulin response.

Example 4

Figure 5:
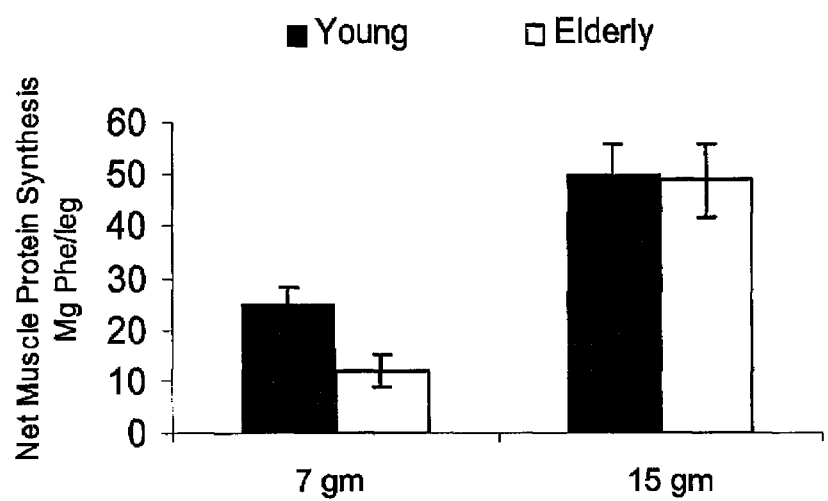
FIG. 5 shows a dose response to an embodiment of a composition for increasing muscle mass, strength, and functional performance in a profile equal to that in whey protein.

Young and elderly (age>65 years) subjects were given either about 7 gm or about 15 gm of EAAs in an embodiment replicating the proportionate contribution of each EAA to the overall content of whey protein. In response to the 7 gm dose, the elderly had a diminished response, with the total rate of synthesis increasing only half as much as in the young. However, the response to 15 g was equivalent in the two groups, as seen in FIG. 5 which shows a dose response to essential amino acids in profile equal to that in whey protein. These results underscore the importance of providing an adequate dose to elicit a robust response in the elderly. The observation was explored in more depth in the following examples.

Example 5

Figure 6:
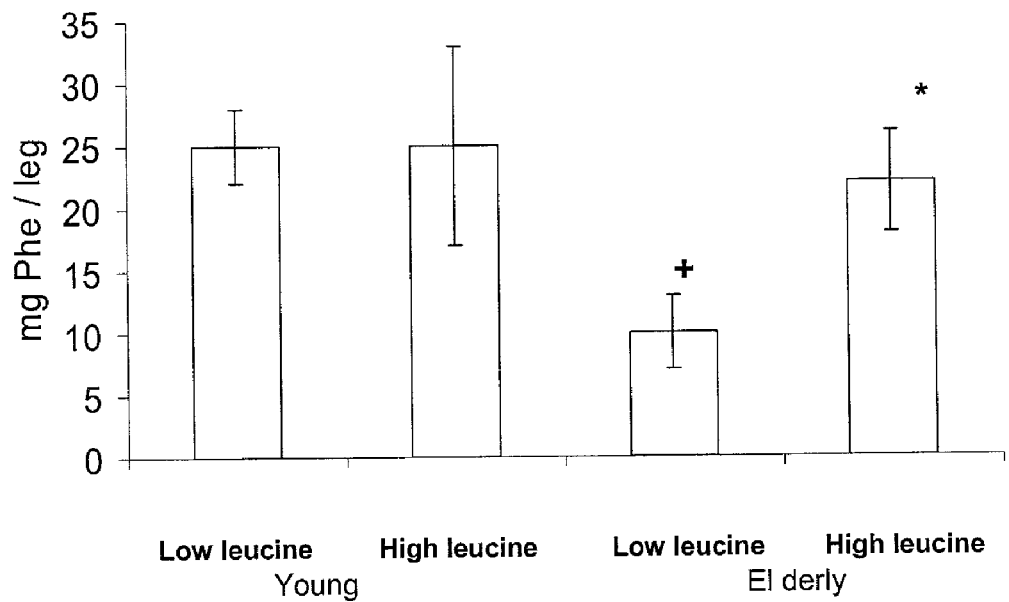
FIG. 6 shows the effect of embodiments of a composition for increasing muscle mass, strength, and functional performance on muscle protein synthesis.
Figure 7:
FIG. 7 shows net phenylalanine uptake after delivery of a composition for increasing muscle mass, strength, and functional performance.

It was hypothesized that there are two components of the mechanism of stimulation of muscle protein synthesis by EAAs: 1) activation of factors involved in the initiation of protein synthesis; and 2) increased availability of precursors. The results presented in FIG. 6 suggest that the responsiveness of the signaling pathways that ultimately activate the initiation of protein synthesis was blunted in the elderly since precursor availability was increased similarly in both young and old. FIG. 6 shows the effect of a composition of EAA mixture on muscle protein synthesis. The dosage was about 7 gm of each mixture; low leucine=26% leucine; high leucine=40% leucine. The * indicates a significant difference from low leucine in the elderly (p<0.05). The + indicates a difference from low leucine in the young. Consequently, the effect of adjusting the composition of the EAA mixture was tested. It was postulated that increasing the proportion of leucine would activate the initiation pathways, so the proportionate contribution of leucine to the total mixture of amino acids was increased from 8 (the proportion in whey protein) to 40 percent. The results are shown in FIG. 7, which shows net phenylalanine uptake (reflecting protein synthesis) 3.5 hours after 15 g EAA (N=7) or 15 g of whey (N=8) in elderly subjects. The * indicates P<0.05 as compared to whey protein, though both increases are significantly greater than fasting uptake.

These results indicate that extra leucine is of no particular benefit in younger subjects. Presumably any benefit in terms of more extensive activation of the initiation process was balanced by the diminished supply of the other EAAs as precursors. In contrast, the principal limiting factor in the elderly was apparently activation of initiation, since the high leucine mixture effective increased the response to about 7 g of EAAs to the same as in the young.

Example 6

Muscle protein synthesis was stimulated in anesthetized rabbits when arginine was increased to about 50% of the total mixture of amino acids infused. Muscle protein breakdown was unchanged when arginine was added to the amino acid solution, meaning that net muscle catabolism was virtually completely reversed in these post-absorptive rabbits. The arginine effect was comparable to the response to increasing the proportion of leucine to about 50% of the total. The mechanism by which arginine activates the initiation of protein synthesis is the same as leucine. Further, arginine is relatively deficient in the elderly. Thus, addition of arginine may work in concert with leucine to activate protein synthesis in elderly.

Example 7

If supplementation entails a nutritional tradeoff of calories, then the supplement must be capable of stimulating net muscle protein synthesis to a greater extent than conventional intake alone. For this reason, the acute response of net muscle protein synthesis (reflected by net phenylalanine uptake) of elderly volunteers to about 15 g EAA supplementation (N=7; 67±2 yrs) and about 15 g of high-quality intact protein (whey; N=8; 69±2 yrs) was reviewed.

Net phenylalanine uptake, an indication of net protein balance, was significantly greater for the EAA group compared to the whey group (P<0.05; 53±10 mg phe/leg EAA vs 21±5 mg phe/leg whey; FIG. 7). Both supplements stimulated muscle protein synthesis (p<0.05), but the increase was greatest in the EAA group. Post-prandial fractional synthetic rates of muscle protein were 0.088±0.011% $hr^{-1}$ for the EAA group, and 0.066±0.004% $hr^{-1}$ for the whey group (p<0.05). The conversion of phenylalanine uptake to mg of protein as described above results in an accrual of 4.0±0.4 g of protein/leg for the EAA supplement, versus 2.2±0.3 g protein/leg for the whey protein, indicating that a 15 g EAA supplement provides a much greater anabolic stimulus than whey protein. Not only was the EAA mixture more effective, but the efficiency of protein utilization (net protein synthesis/protein [i.e., AA] ingestion) was approximately 1.1 for the EAA mixture as opposed to approximately 0.2 for whey protein. The four-fold higher ratio for the EAAs reflects an efficient reutilization of non-essential amino acids that otherwise would have been excreted. This ratio also reflects the optimal formulation of an EAA mixture to match the requirement for muscle protein synthesis. In addition to supporting the general hypothesis underlying this proposal, these results show that the principal effect of exogenous AAs is on muscle protein synthesis as opposed to breakdown. Thus, ingestion of an EAA supplement between meals may reduce periods of post-prandial catabolism and provide frequent stimulation of muscle protein synthesis.

Example 8

Figure 8:
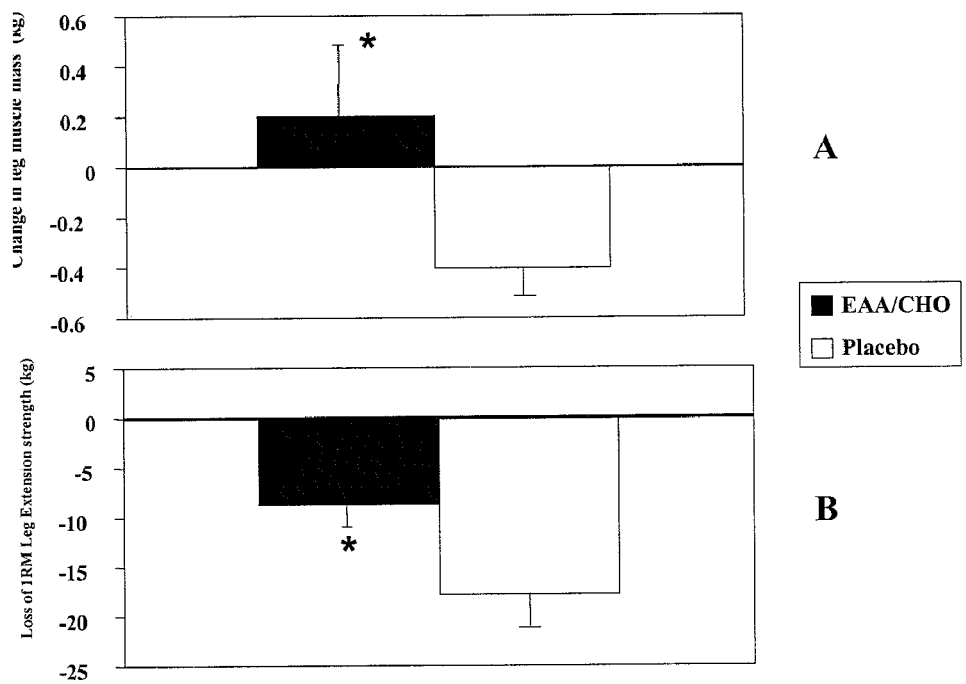
FIG. 8 shows the effects of an embodiment of a composition for increasing muscle mass, strength, and functional performance on lean body mass and preservation of muscle function.

Since muscle protein synthesis decreases with inactivity, we proposed that EAA could restore the synthetic capacity of muscle during bed rest. The hypothesis was that repeated nutritional stimulation of skeletal-muscle protein synthesis throughout 28 days of bed rest would ameliorate the loss of LBM and preserve muscle function. One group of young, healthy volunteers (n=7) received a supplement of about 15 g of EAAs plus about 30 g glucose three times each day, while the other group (n=6) received a placebo drink. The results indicated that the EAA drink was capable of stimulating net muscle protein synthesis throughout the 28 days of inactivity. In comparison, ingestion of a conventional meal replacement drink clinical meal (Boost) was minimally effective in stimulating muscle anabolism, especially after inactivity. The peak response of muscle net balance to the EAA plus glucose supplement was almost six-fold greater than the response to Boost. The repeated stimulation of muscle protein synthesis translated to maintenance of LBM (FIG. 8A). Further, preservation of LBM ameliorates the loss of muscle function (FIG. 8B) with prolonged bed rest. The placebo group's muscle mass of both legs (estimated by dual-energy x-ray absorptiometry [DEXA] analysis) decreased significantly (approximately 438±135 g per 28 days; FIG. 8A). In contrast, the leg muscle mass demonstrated a non-significant increase of 210±125 g in the supplemental trial, meaning a difference from one trial to the other of approximately 650 g muscle/28 days. Thus, FIG. 8 shows that an essential amino acid (EAA) supplement maintains lean body mass (by DEXA, Panel A) after 28 days of bed rest in 7 subjects (P<0.05). Muscle function is preserved to a greater extent (Panel B) in the EAA group compared to the placebo group (N=6; P<0.05).

Figure 9:
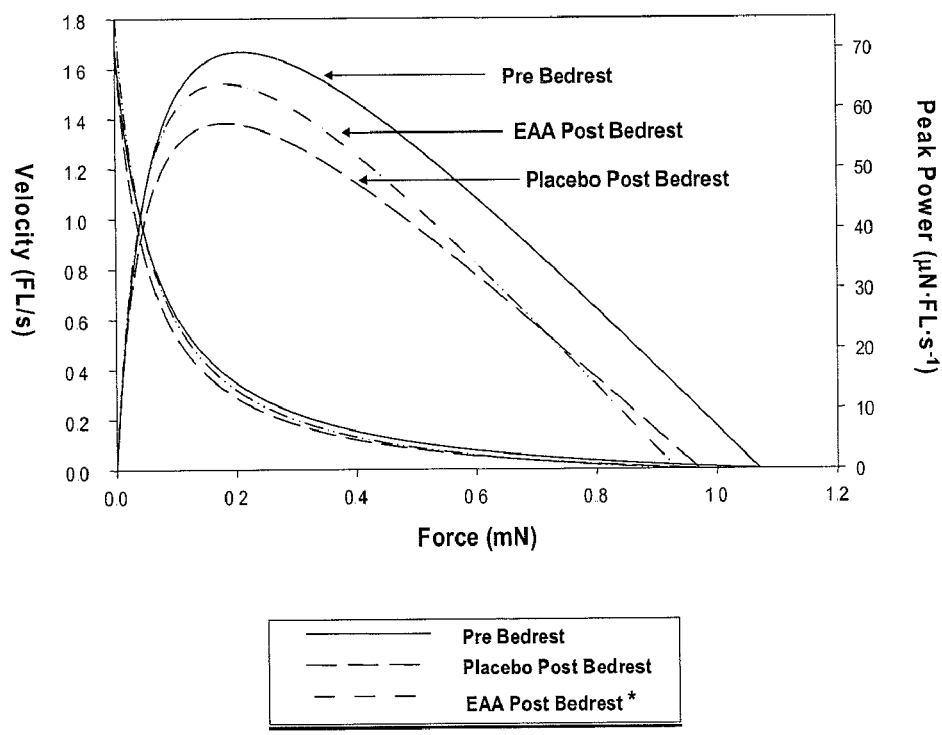
FIG. 9 shows muscular shortening velocity and peak power maintained after delivery of an embodiment of a composition for increasing muscle mass, strength, and functional performance.

The effect of EAA+glucose was also evident at the single fiber level. After 28 d of supplementation in 7 subjects, the EAA+glucose supplement prevented the bed rest-induced depression of peak power and shortening velocity in the fast type II fiber (FIG. 9). FIG. 9 shows shortening velocity (fiber length (FL)/sec; P<0.01) and peak power (µN/FL/sec; P0.05) are maintained in subjects given an EAA supplement (N=7) versus placebo (N=6) While the placebo group demonstrated a decrease in single fiber peak power from pre bed rest (57.6±2.5 vs 69.5±3.5 µN/fiber length (FL)/sec; P<0.05), peak power was maintained in the EAA group (63.9±3.9 µN/FL/sec). Further, shortening velocity was maintained at pre-bed rest levels in the EAA group (0.346±0.015 FL/sec vs 0.323±0.013 FL/sec pre-bed rest; P<0.01). Thus, this data indicates that EAA maintains muscle function at the single fiber level, and that this translates to an increase in function at the whole-muscle level.

These findings highlight two important points. First, supplementation with EAAs+glucose in young, healthy volunteers ameliorated the loss of muscle mass resulting from prolonged inactivity. Second, the repetitive stimulation of muscle protein turner by the dietary supplement resulted in improvement in muscle function at the single fiber level, which translated to an amelioration of the loss of strength at the physiological level.

Example 9

Twelve individuals over the age of 62 were given embodiments of essential amino acid supplements twice per day for 8 weeks. The composition of the supplement is shown in Table 1.

TABLE 1

Composition of the EAA Supplement.

| Amino acid | Amount (g) | % Total |
|---|---|---|
| Histidine | 1.64 | 10.88 |
| Isoleucine | 1.56 | 10.34 |
| Leucine | 2.79 | 18.50 |
| Lysine | 2.30 | 15.25 |
| Methionine | 0.46 | 3.05 |
| Phenylalanine | 2.30 | 15.25 |
| Threonine | 2.20 | 14.59 |
| Tryptophan | 0.10 | 0.66 |
| Valine | 1.73 | 11.47 |
| Total | 15.08 g | 100.00 |

Subjects (n=12) were greater than 62 years (mean=65.6±2.8). Five of the subjects were male and five were female. On the basis of the dietary and activity records, which were kept throughout, two subjects were dropped. In one case the dietary protein intake changed by approximately 40%, and in the other case the activity level changed drastically as the subject began an organized exercise program.

After initial screening and acceptance into the study, subjects reported to the Clinical Research Center (CRC) for pretesting. They were then given the supplement dosages in pre-packaged form. They were instructed to take the capsules between breakfast and lunch and between lunch and dinner, and to return the empty single-dose containers, along with a log book documenting when they took the capsules. The subjects reported back to the CRC at 4 weeks and 8 weeks for retesting.

Regarding compliance, subjects had no problems ingesting the capsules. However, two subjects did not comply with instructions to maintain constant dietary intake (1 subject) or activity level (1 subject), and were subsequently dropped from the study Thus compliance was 83%.

Regarding lean body mass, total lean body mass increased in all subjects, the average increase being 1.4±0.3 Kg (mean±SEM) (p=0.025). Similarly, leg lean mass also increased on average of 0.5±0.01 Kg (p=0.0045). There was no discernable effect of initial lean mass or gender on the magnitude of response.

Regarding leg strength, the overall average (all subjects) leg strength increased from 134, 3±21.8 at baseline to 149.9±19.9 (mean±SEM) (p=0.0076).

A variety of function tests were performed. The subjects were not screened to be frail. As a result, performance on some of the tests was close to maximum before the study started. For example, scores on the Short Physical Performance Battery (SPPB) test averaged 11.6±0.3 (mean±SEM) before the start of the study Since the maximum value is 12, there was insufficient room for improvement to expect any treatment effect. Significant positive effects of EAA supplementation were observed on function tests in which there were no maximum values. There was an increase in walking speed after EAA supplementation of 0.12±0.015 m/s (mean±SEM) from the basal value of 1.26±0.015 m/s (mean±SEM) (p=0.002).

In all cases in which statistically significant effects of EAA supplementation were observed, there was a significant correlation between the starting value and the magnitude of impact of the treatment. For example, the weaker the subject at the start of the study, the greater the gain in strength with EAAs, etc.

It was therefore concluded that supplementation of normal dietary intake with two doses of 11 g of essential amino acids increased muscle mass, strength, and physical function in healthy elderly subjects.

Example 10

The lack of responsiveness to the potential anabolic action of insulin in elderly makes a supplement that elicits a high insulin response undesirable. Nonetheless, there is a need for energy to fuel the protein synthetic response. The exact energy cost can be calculated. The calculation of the estimated energy expenditure due to stimulation of muscle protein synthesis following EAA ingestion is based on the average leg muscle mass (LMM) of elderly of 6 kg, The muscle in one leg represented approximately 20% of the total muscle mass and about 26% of the leg LMM is protein-bound amino acids. To calculate the total rate of muscle protein synthesis, previous work had revealed the fractional synthetic rate of muscle protein increased by an average of 0.03/h following the ingestion of 15 grams of EAAs. To calculate the energy cost of muscle protein synthesis, it was assumed that (1) on average 1 mole of amino acids (AA)=150 g of AA; (2) the cost of synthesizing 1 mol of AA equals 4 ATP; and (3) the hydrolysis of 1 mol of ATP releases 20 Kcal of energy. The formulae are expressed as:

$$\text{Total bound } AA \text{ content of muscle(gm)} = \text{Leg } LMM \text{ (grams)} \times 5 \times 0.26 \quad (1)$$

$$\text{Incorporation of } AAs \text{ into muscle protein(gm/h)} = (1) \times FSR(1/h) \quad (2)$$

$$\begin{aligned}&\text{Energy cost of stimulated muscle protein synthesis}\\&(\text{Kcal/h}) = 2 \times 1 \text{ mol protein-bound amino acids/}\\&150 \text{ g muscle} \times 4 \text{ mol } ATP/\text{mol protein-bound}\\&\text{amino acids} \times 20 \text{ Kcal/mol } ATP\end{aligned} \quad (3)$$

These calculations indicate that the protein synthetic response to EAAs requires about 108 Kcal of energy. This amount of energy can be provided in approximately 27 g of carbohydrate.

Example 11

Figure 10:
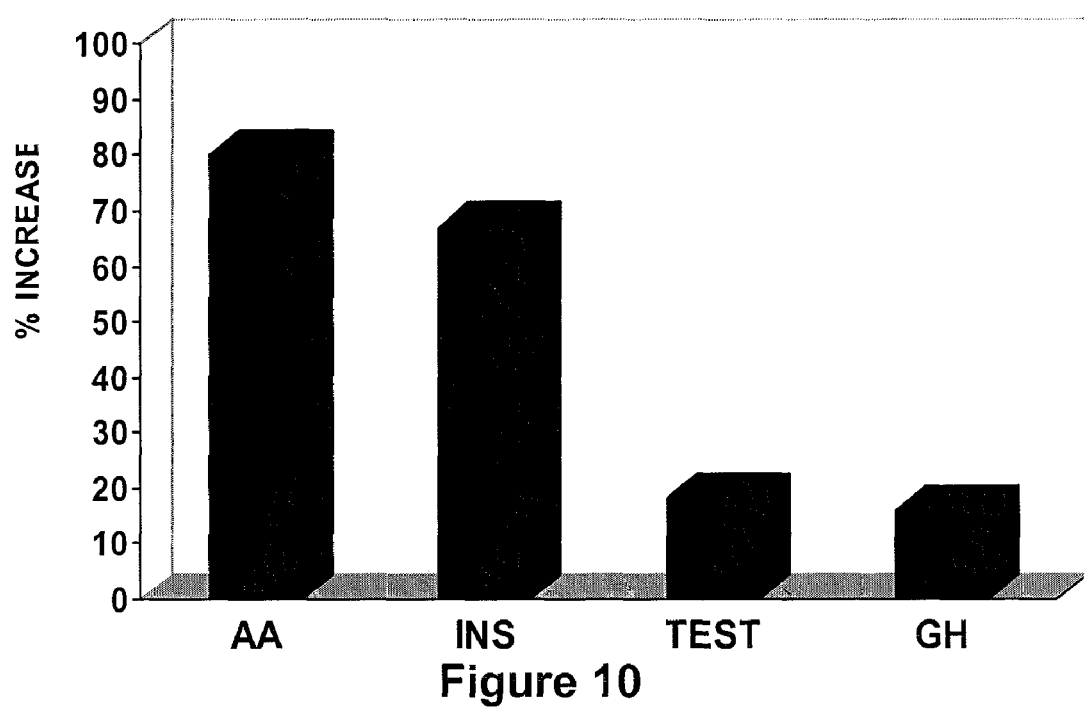
FIG. 10 shows a comparison of increase in muscle protein synthesis after ingestion of a single dose of an embodiment of composition for increasing muscle mass, strength, and functional performance with a pharmacological treatment with insulin, testosterone and growth hormone.

A variety of studies have employed pharmacological treatments increase muscle mass and strength in the elderly. The most potent have been the hormone testosterone (in men), growth hormone, and insulin. The insulin effect was the only one in the same range of effectiveness as EAAs. However, the results with insulin were in a very tightly controlled laboratory setting in which glucose was infused simultaneously to maintain euglycemia. This approach is not practical in a free-living setting, so the relevant comparisons are between EAAs and testosterone and growth hormone. The EAA effect is the largest, as shown in FIG. 10, which shows a comparison of increase in muscle protein synthesis after ingestion of a single dose of 15 g of EAAs with the pharmacological treatment with insulin, testosterone and growth hormone.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

Example 12

Figure 11:
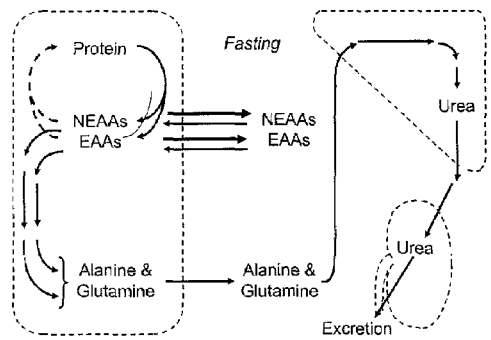
FIG. 11 shows nitrogen flux between liver and muscle during a fasting state.

In the fasting situation there is a constant cycling of both EAAs and non-essential amino acids (NEAAs) from protein into the intracellular free amino acid pool and back into protein. FIG. 11 shows nitrogen flux between liver and muscle during a fasting state. However, a fraction of the amino acids released as a result of protein breakdown are metabolized, with the resultant production of alanine and glutamine. There is also a net release of EAAs and the other NEAAS into plasma. Alanine and glutamine serve as the principal forms in which the nitrogen (N) from the metabolized amino acids is transported back to the liver for eventual incorporation into urea and subsequent excretion.

Figure 12:
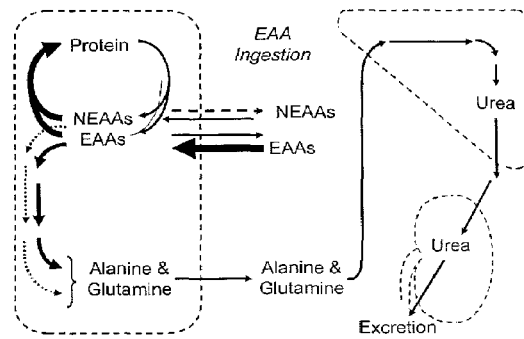
FIG. 12 shows nitrogen flux between liver and muscle related to delivery of an embodiment of composition for increasing muscle mass, strength, and functional performance.
Figure 13:
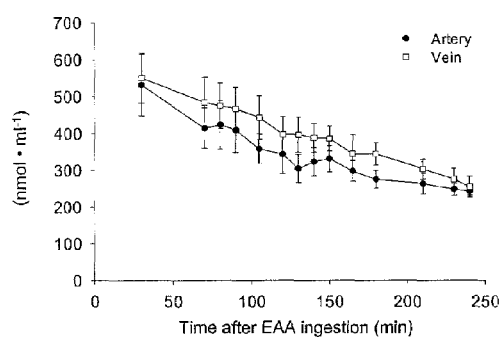
FIG. 13 shows alanine concentration after delivery of an embodiment of composition for increasing muscle mass, strength, and functional performance.
Figure 14:
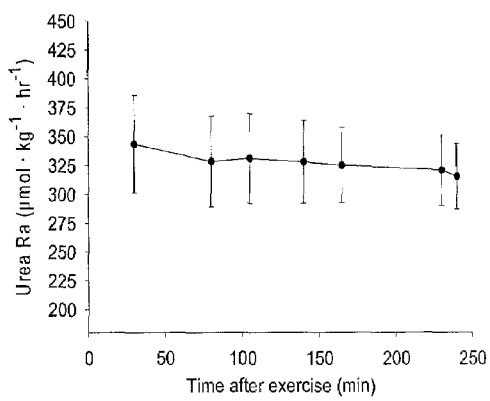
FIG. 14 shows urea production after delivery of an embodiment of composition for increasing muscle mass, strength, and functional performance.

Following ingestion of EAAs the situation is altered by the net uptake of EAAs. FIG. 12 shows nitrogen flux between liver and muscle following EAA ingestion. This results in the stimulation of synthesis. Since NEAAs are required for the synthesis of new protein, the NEAAs released from protein breakdown will be recycled back into protein at a greater rate, meaning that less will be released into plasma. Alanine and glutamine concentrations thus fall; this effect on alanine concentration after ingestion of boluses of 6 gm each of EAAs at time 0 and 60 min. is shown in FIG. 13. Since alanine and glutamine are the principal precursors of urea production, urea production does not increase following EAA ingestion, as shown in FIG. 14. This is in contrast to the response to ingestion of intact protein, such as whey protein, whereby increased N intake results in increased production of urea and burden on the kidney for excretion.

The invention claimed is:

1. A composition of matter for increasing muscle mass, strength, and functional performance, comprising:
   an amino acid component, said amino acid component including:
      at least 11 percent by mass leucine; and
      at least one other amino acid, said amino acid selected from the group consisting of: histidine, isoleucine, valine, lysine, methionine, phenylalanine, threonine, arginine, glycine, carnitine, and citrullene;
   a carbohydrate; and
   creatine.

2. The composition of claim 1 wherein said amino acid component comprises: leucine histidine, isoleucine, valine, lysine, methionine, phenylanlanine, threonine, glycine and arginine.

3. The composition of claim 1 wherein said amino acid component comprises: leucine histidine, isoleucine, valine, lysine, methionine, phenylalanine, threonine, glycine and citrullene.

4. The composition of claim 1 wherein said carbohydrate comprises ribose.

5. The composition of claim 1 wherein said leucine comprises a percentage of said amino acid component by mass less than 20 percent.

6. The composition of claim 1 wherein said composition is a component of means for liquid administration.

7. The composition of claim 1 further comprising an excipient.

8. A method of increasing muscle mass, strength, and functional performance, comprising:
   having a patient; and
   delivering to said patient a composition of matter comprising
   an amino acid component, said amino acid component including:
      at least 11 percent by mass leucine; and
      at least one other amino acid, said amino acid selected from the group consisting of: histidine, isoleucine, valine, lysine, methionine, phenylalanine, threonine, arginine, glycine, carnitine, and citrullene;
   a carbohydrate; and
   creatine.

9. The method of claim 8 wherein said patient is elderly.

10. The method of claim 8 wherein said delivering is oral.

11. The method of claim 10 wherein said delivering is by liquid administration.

12. The method of claim 8 wherein said leucine comprises a percentage of said amino acid component by mass less than 20 percent.

13. The method of claim 8 wherein said composition further comprises an excipient.

14. The method of claim 8 wherein said carbohydrate comprises ribose.

15. A method of increasing muscle mass, strength, and functional performance in the elderly, comprising:
   generating a composition of matter comprising:
      an amino acid component, said amino acid component including:
         at least 11 percent by mass leucine; and
         at least one other amino acid, said amino acid selected from the group consisting of: histidine, isoleucine, valine, lysine, methionine, phenylalanine, threonine, arginine, glycine, carnitine, and citrullene;
      a carbohydrate; and
      creatine;
   providing to an elderly patient said composition of matter.

16. The method of claim 15 wherein said leucine comprises a percentage of said amino acid component by mass less than 20 percent.

17. The method of claim 15 wherein said providing is oral.

18. The method of claim 15 wherein said providing is by liquid administration.

19. The method of claim 15 wherein said carbohydrate comprises ribose.

20. A composition of matter for increasing muscle mass, strength, and functional performance, comprising:
   an amino acid component, said amino acid component including:
      leucine in an amount above that occurring in whey protein; and
      at least one other amino acid; and
   a carbohydrate.

21. The composition of claim 20 wherein at least one of said at least one other amino acid is selected from the group consisting of: histidine, isoleucine, valine, lysine, methionine, phenylalanine, threonine, arginine, glycine, carnitine, and citrullene.

* * * * *